United States Patent [19]

Amundson

[11] 4,156,429

[45] May 29, 1979

[54] IMPLANTABLE ELECTRODE

[75] Inventor: David C. Amundson, St. Paul, Minn.

[73] Assignee: Cardiac Pacemakers, Inc., St. Paul, Minn.

[21] Appl. No.: 840,577

[22] Filed: Oct. 11, 1977

Related U.S. Application Data

[63] Continuation-in-part of Ser. No. 758,583, Jan. 12, 1977, abandoned.

[51] Int. Cl.² ............................................. A61N 1/04
[52] U.S. Cl. ................................................ 128/419 P
[58] Field of Search .................... 128/404, 418, 419 P

[56] References Cited

U.S. PATENT DOCUMENTS

| | | | |
|---|---|---|---|
| 3,178,280 | 4/1965 | McGee et al. | 75/200 |
| 3,911,928 | 10/1975 | Lagergren | 128/418 |
| 3,981,309 | 9/1976 | Cannon | 128/404 |
| 4,011,861 | 3/1977 | Enger | 128/419 P |

*Primary Examiner*—William E. Kamm
*Attorney, Agent, or Firm*—Orrin M. Haugen; Thomas J. Nikolai

[57] ABSTRACT

An improved implantable electrode for delivery of electrical stimulation pulses or signals to an organ such as the heart from an electrical pulse generator. The electrode is normally exposed to the organ to be stimulated and is, in turn, electrically coupled to a conductive lead extending from the pulse generator, with the electrode being a body which substantially completely envelopes the lead. The electrode comprises a plurality of electrically conductive metallic filaments compressed together to form a generally fibrous body which may in certain instances be pliant or flexible in nature. The filaments preferably have a mean, effective diameter less than about 100 microns and form from about 3% to 30% of the total volume of the fibrous member, and preferably from 5% to 20%. In one embodiment, the filaments are retained as a bundle within a metallic grid enclosure.

6 Claims, 8 Drawing Figures

IMPLANTABLE ELECTRODE

CROSS-REFERENCE TO RELATED APPLICATION

This is a continuation-in-part of application Ser. No. 758,583, filed Jan. 12, 1977 and entitled "IMPLANTABLE ELECTRODE", now abandoned, the application having been assigned to the same assignee as the present application.

BACKGROUND OF THE INVENTION

The present invention relates generally to an improved implantable electrode for delivering electrical stimulation pulses to an organ, and more particularly to an improved implantable electrode means for delivery of electrical stimulation pulses to the heart.

Heart pacer therapy and technology has expanded intensively, and with improvements available in batteries and circuitry, a need has now arisen for improvement of the functional characteristics of the electrode. Recent improvements in batteries and a corresponding reduction of current consumption of the circuitry within the pulse generator have made it both desirable and necessary to improve electrode performance, particularly improvements relating to the current requirements of the electrode. Furthermore, most of the complications resulting from heart pacer therapy may be traced to the electrodes, and thus physical properties appear to also require improvement.

Studies have been conducted, and certain improvements in electrodes and leads have been made in the past. Specifically, metal fatigue has presented problems which may result in lead fractures. Furthermore, improved lead sealing and electrode geometries have been developed, with one typical lead structure being disclosed in co-pending application Ser. No. 635,909, filed Nov. 28, 1975, now U.S. Pat. No. 4,033,355, and entitled "Electrode Lead Assembly for Implantable Devices", assigned to the same assignee.

Porous electrode structures have been known in the past, with the pores being formed in a solid structure and having a size of less than approximately 100 microns. Such structures have been of assistance, particularly in the compatibility of the porous structure to accommodate ingrowth into the channels of active heart tissue. Further improvements are available from the electrode structure of the present invention, with these improvements including both electrical performance and accommodation of desirable heart tissue ingrowth. In electrical performance, improvements are found particularly in the reduction of polarization. Stimulation thresholds have been significantly reduced, with those of the present structure having been found to be as low as one third to one half of the requirements of conventional electrodes. The electrode of the present invention consists of a filamentary member, wherein the individual filaments may be compressed together to form a substantially solid body, and wherein the filaments preferably have a diameter of less than about 100 microns and form less than approximately 20% of the entire volume of the filamentary or fibrous electrode. In one embodiment, the individual filaments may be compressed of compacted within a grid enclosure, with the individual elements forming the grid being slightly larger than the filaments forming the confined filamentary electrode, with the grid enclosure being adapted to confine, restrict, or otherwise retain the filamentary electrode intact.

Organ stimulation, particularly heart stimulation, may be described in terms of electrical field theory. Excitation is initiated by virtue of an electrical stimulus which exceeds a certain threshold level. The electrical field, therefore, may be characterized as a force being applied to the system. Relating the field strength to the electrode structure, the maximum field strength is believed to be present at the surface of the electrode, with the magnitude of the field being generally inversely proportionally to the electrode size. In ordinary electrodes, the excitable tissue normally becomes spaced from the surface of the electrode by the growth of a barrier or layer of fibrotic material. Accordingly the field strength must be related to that field which is available or effective at the interface which develops between the excitable tissue and the fibrotic tissue. Hence, any reduction in the formation or growth of fibrotic tissue should reasonably be calculated to increase the magnitude of the effective field at the excitable tissue boundary and thus increase the ultimate effectiveness of the electrode.

Furthermore, in normal heart pacers, particularly those of the demand/inhibit type or those which respond in synchrony to a natural heart signal, the electrode performs a sensing function as well as a stimulation function. The sensing impedance of the amplifiers typically used range in the order to 20,000 ohms, and any source impedance will, of course, be in series with the input impedance. The electrode of the present invention permits the source impedance to remain low, thereby enhancing the overall sensing capability of the electrode. As has been indicated, the polarization is exceptionally low, this being believed to be due to the large real surface area available for polarization considerations. However, it has also been found that the effective surface area of the structure is small for stimulation considerations. This appears to provide significant advantages for both operating parameters.

SUMMARY OF THE INVENTION

Turning now to the aspects of the present invention, the implantable electrode consists of a compressed or compacted bundle of metallic filaments or fibers, with the bundle being designed so as to substantially completely envelop the surface of the conductive lead which couples the pulse generator to the electrode. The individual fibers or filaments forming the fibrous member have a diameter of between about 10 microns and 100 microns, with the preferred diameter being about 20 microns. The preferred filamentary diameter of 20 microns is due to the general match of the cell size with the filament size, with cell size bieng generally in the area of about 20 microns.

The solid filamentary material forms between about 3% to 30% of the volume of the member, with the lower ranges, such as approximately 5% being preferred. The balance of the volume of the fibrous member is, of course, open. When less than about 3% of the volume is formed of the filamentary material, the structure appears to become overly porous, and when more than about 20% of the volume of the member is formed of the filamentary material, the finished structure appears to become generally quasi solid and may in some cases become somewhat less pliant in those devices wherein this is a desired feature.

As a result of this structural design, it has been found that substantially less energy is required for stimulation of the heart. A reduction in polarization occurs, thereby further enhancing the performance of the electrode and reducing the energy required for constant and consistent organ stimulation over extended periods of time. Ingrowth occurs between the surrounding tissue and the electrode, thereby improving electrical response, and furthermore enhances the performance of the device by reducing the tendency toward dislodgement while also reducing abrasion.

Therefore, it is a primary object of the present invention to provide an improved implantable electrode structure which is particularly adapted for use in the electrical stimulation of an organ, such as the heart, with the electrode comprising a metallic filamentary bundle.

It is a further object of the present invention to provide an improved implantable electrode means in the form of a fibrous tip member consisting of a filamentary probe which is arranged to be electrically coupled to a remotely disposed pulse generator, and being designed to substantially completely envelop the electrically conductive member which extends from the pulse generator to the electrode.

It is yet a further object of the present invention to provide an improved implantable electrode means for use with heart pacemakers, wherein the electrode is formed as a bundle or compress of metallic fibers, and wherein the metallic fibers have a diameter of less than about 100 microns and form between 3% and 30%.

Other and further objects of the present invention will become apparent to those skilled in the art upon a study of the following specification, appended claims and accompanying drawings.

DESCRIPTION OF THE PREFERRED EMBODIMENTS

In accordance with one of the alternate preferred embodiments of the present invention, and with particular attention being directed to FIGS. 2-5 of the drawings, it will be seen that the cardiac pacer assembly generally designated 10 includes a pulse generator with lead assembly 14 extending from the coupling zone or station 12 to the conductive electrode 15. Conductive electrode 15 is, of course, exposed and is generally in physical contact with the tissue to be stimulated, such as the heart muscle in the case of a cardiac pacer device. It will be understood that the configuration of the electrode as illustrated at 15 is merely one of many such designs, with the arrangement being appropriately adapted for either myocardial or epicardial type electrodes.

Figure 1:
FIG. 1 is a flow diagram of a typical procedure which may be employed in the preparation of the implantable electrode means of the present invention.
Figure 2:
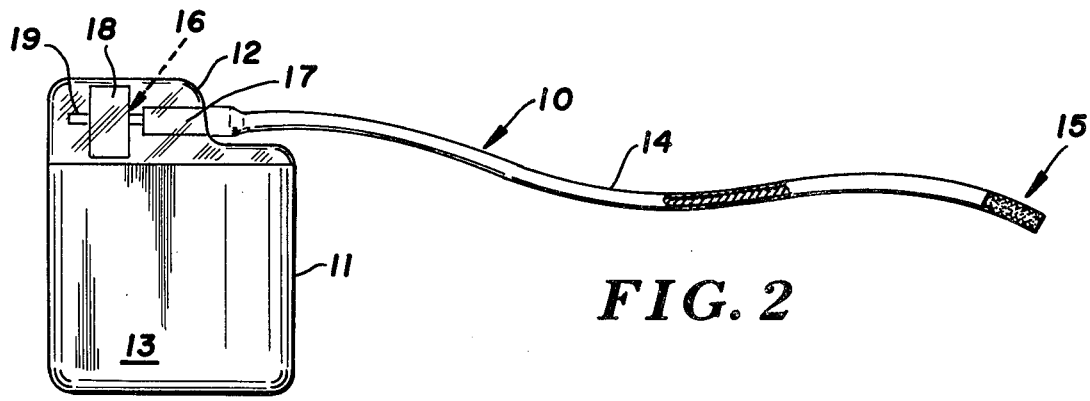
FIG. 2 is a side elevational view illustrating one typical embodiment of an implantable electrode means of the present invention in combination with a typical pulse generator and conductive lead assembly.

The arrangement of the device illustrated in FIG. 2 is that of a unipolar cardiac pacer, and the assembly may be in the form of that assembly disclosed and claimed in U.S. Pat. No. 3,882,707. The circuitry for the pulse generator 13 may be in the form of that circuitry disclosed in U.S. Pat. No. 4,041,953.

It will be appreciated, of course, that bipolar leads may be prepared utilizing the features of the present invention. For purposes of comprehending the concept, however, a unipolar device is disclosed for simplicity.

Figure 3:
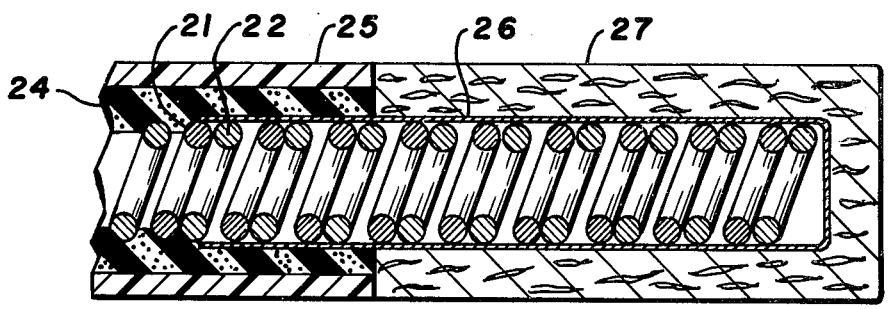
FIG. 3 is a sectional view on an enlarged scale taken through the diameter of one embodiment of the lead and electrode, and illustrating one manner in which the electrode may be secured to the conductive lead.
Figure 4:
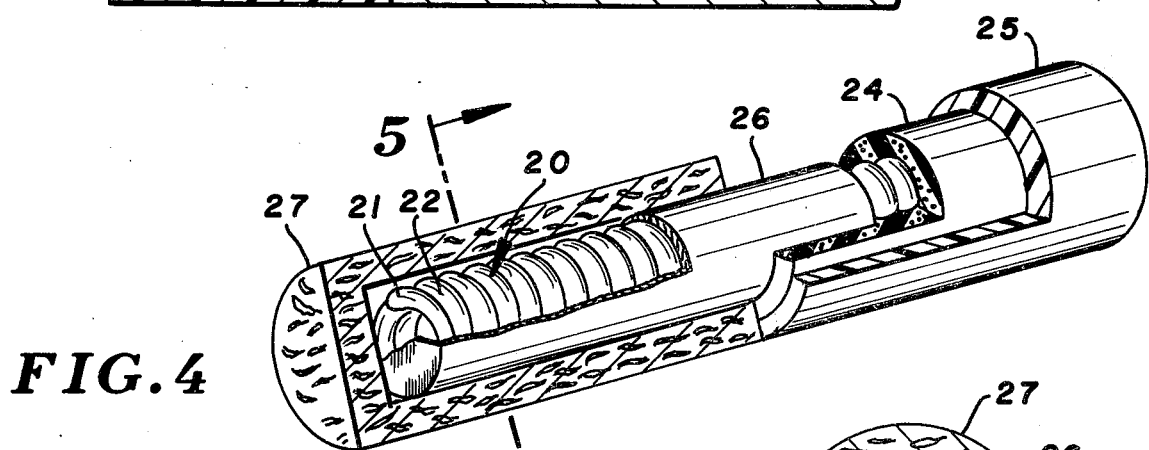
FIG. 4 is a perspective view, partially broken away, and further illustrating the manner in which the implantable electrode of FIG. 3 is coupled to the conductive lead.
Figure 6:
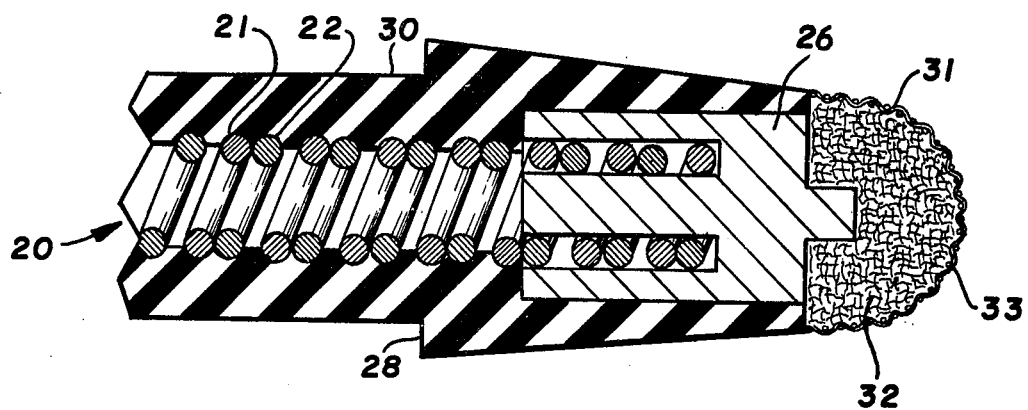
FIG. 6 is a sectional view on an enlarged scale from FIG. 2, and illustrating an alternate preferred embodiment of the lead and electrode, and illustrating the details of the alternate preferred embodiment.
Figure 7:
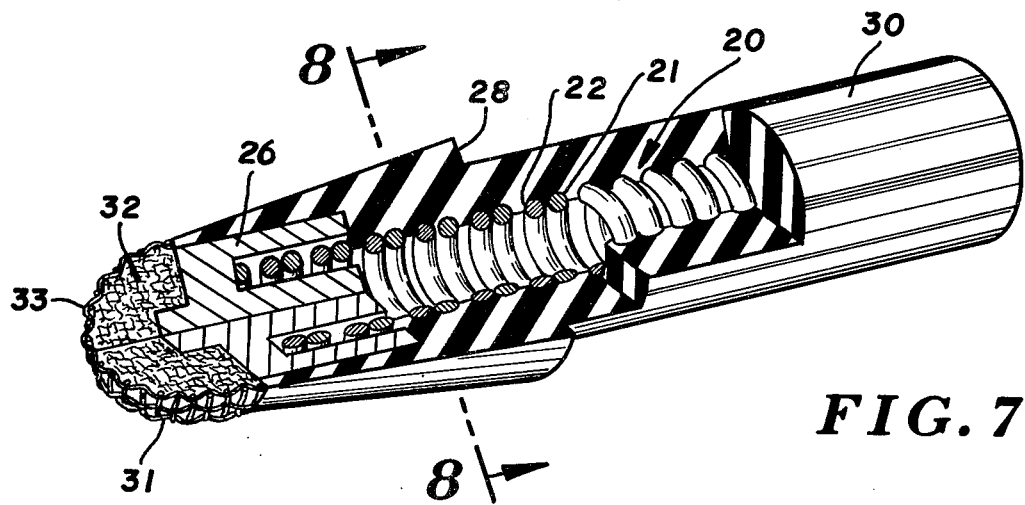
FIG. 7 is a perspective view, partially broken away, and further illustrating certain details of the embodiment of FIG. 6, and the manner in which the electrode is coupled to the conductive lead.
Figure 8:
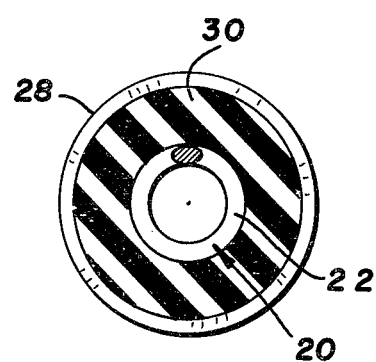
FIG. 8 is a sectional view taken along the line and in the direction of the arrows 8—8 of FIG. 7.

Attention is now directed to FIGS. 3 and 4 of the drawings which illustrate the details of the lead assembly and the manner in which the implantable electrode is secured thereto. Specifically, as illustrated in FIG. 3, the conductor system generally designated 20 includes a pair of parallel spans 21 and 22, each of which is arranged in a helical pattern about a common axis. The coiled conductors have a uniform outer diameter, as is apparent in the structure shown in FIGS. 3 and 4. A pair of coaxially disposed tubular insulating sheaths 24 and 25 are illustrated to enclose the coiled conductors 21 and 22, it being appreciated, of course, that a single insulating sheath such as illustrated in the embodiment of FIGS. 6-8 inclusive may be employed as well. If desired, a double insulating sheath, such as is illustrated in FIG. 3 may be employed, with such an arrangement being disclosed in U.S. Pat. No. 4,033,335.

Figure 5:
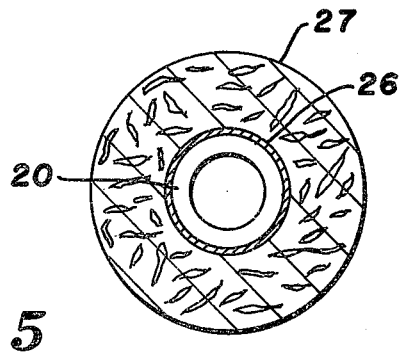
FIG. 5 is a sectional view taken along the line and in the direction of the arrows 5—5 of FIG. 3.

In the embodiment illustrated in FIG. 3-5 inclusive, electrode 15 is shown coupled electrically and mechanically to the outer circumference of the coil formed by helically wound conductors 21 and 22. In order to seal the lead assembly, a conductive cap member is provided, as shown at 26, with the filamentary metallic compress 27 being secured both electrically and mechanically to the outer surface thereof. It will be appreciated that other sealing techniques may be employed as desired.

Attention is now directed to FIGS. 6-8 of the drawings wherein the other of the alternate preferred embodiments is illustrated. Specifically, the conductor system, against generally designated 20, (this being designated with the same reference numeral as has been utilized in the corrresponding component of FIG. 3) includes a pair of parallel spans 21 and 22, each of which is arranged in a helical pattern about a common axis, as is true in the alternate embodiment of FIGS. 3 and 4. A tubular insulating sheath 30 having an enlarged portion forming an abutment surface 28 near the end, with insulating sheath 30 enclosing the coiled conductors 21 and 22.

In the embodiment illustrated in FIGS. 6-8 inclusive, electrode 31 is shown coupled electrically and mechanically to the outer circumference of the coil formed by helically wound conductors 21 and 22. Electrode 31 includes a bundle of filamentary fibers 32, enclosed within a metallic grid 33 of a composition similar to that of the filaments forming the enclosed bundle.

For materials of construction, it will be appreciated that platinum is preferred, with other substances being suitable such as, for example, Elgiloy, titanium, or platinum-iridium alloys. Both Elgiloy and 90:10 platinum-iridium alloys are widely used as materials of construction for implantable electrodes.

The material of construction for conductors 21 and 22 is preferably MP35N, nickel-chromium-cobalt alloy, this material being inert to body fluids, and possessing mechanical properties which include the requisite flexural characteristics, tensile strength, and resistance to fatigue.

PREPARATION OF IMPLANTABLE ELECTRODES

In order to prepare the implantable electrode, such as fibrous member 27, a bundle of metallic filaments of platinum are compressed together to form a substantially solid body, and prepared for sintering. The compress is placed within a suitable cavity or chamber, and heated to a temperature of 1500° C. for a period of about 2 hours. This raises the temperature of the metal sufficiently so as to provide substantial vapor pressure for the platinum, and thus form the desired cohesive compress. The diameter of the individual filaments is, in this example, 18 microns, although filament diameters ranging from between about 10 microns and 100 microns may be suitably employed. As a further consideration, the volumetric parameters provide for the structure to be preferably 95 percent open, with the metallic filaments forming the balance of 5% of the volume. It has been found, however, that up to approximately 20% of the volume may be metallic filaments.

In order to prepare the implantable electrode of the embodiment illustrated in FIGS. 6-8, a bundle of metallic filaments of platinum are compressed together to form a substantially solid bundle, and the bundle is then placed within the confines of the grid enclosure. Specifically, the grid enclosure is formed of the same material as the metallic filaments, and normally has a reticulated pattern of 150×150 filaments per inch, with each filament having a diameter of 0.001 inches. In certain instances, a grid having somewhat larger diameter lines may be employed, such as up to approximately 0.002 inches, with one such grid having filament 0.0017 inches in diameter being commercially available. In this embodiment, the bundle is approximately 90% open, with the metallic filaments forming the balance of 10% of the volume. Stated another way, the material is 10% dense. The individual filaments forming the bundle have a diameter of from between about 10 microns and 100 microns, although in the specific example, the filaments have a diameter of 20 microns.

In order to form a solid compress or bundle, the filaments within the grid enclosure are heated to a temperature of 1500° C. for a period of about 2 hours to permit sintering to occur.

As has been indicated, the metallic filament structure of the present invention contributes to a reduction of fibrosis. The reduction is believed due to the utilization of the small diameter metallic filament, together with the provision of permitting approximately 80% or more of the structure to be open. The organ being stimulated provides certain ingrowth into the electrode element, with the ingrowth contributing to a reduction in abrasion, and a more uniform electrical response and function. Therefore, the active heart tissue is disposed more closely adjacent to the surface portions of the electrode which generate the field which performs the actual stimulation. Furthermore, polarization during stimulation is substantially reduced, with measurements indicating that polarization is almost eliminated for most normal cardiac pacer functions. In addition, the sensing function is performed effectively by the structure of the present invention.

While the utilization of a non-woven filamentary mass is contemplated and discussed herein, it will also be appreciated that a woven or knitted pattern may also be employed to form the overall structure. In such an arrangement, the parameters of filament size and volume considerations remain as set forth above.

While various techniques may be employed to bond the electrode structure to the conductive leads, it has been found that diffusion bonding is generally preferred. This is particularly desirable or applicable to the structure illustrated in FIGS. 6-8.

I claim:

1. An implantable electrode means for electrical stimulation of an organ from an electrical signal generator and including an electrically conductive lead member extending from said electrical signal generator to said implantable electrode means and having a surface in electrical contact with said implantable electrode means, said implantable electrode means comprising a plurality of electrically conductive metallic filaments retained together as a bundle to form a compress, with the filaments forming the compress having a diameter of less than about 100 microns and forming between 3% and 30% of the volume of said compress.

2. The implantable electrode means as defined in claim 1 being particularly characterized in that a grid enclosure is provided and wherein said filamentary compress is retained within said grid enclosure.

3. The implantable electrode means as defined in claim 2 being particularly characterized in that said grid enclosure is formed on the same metallic substance as said metallic filaments.

4. The implantable electrode means as defined in claim 1 being particularly characterized in that said filaments form approximately 5% of the volume of said compress.

5. The implantable electrode means as defined in claim 1 being particularly characterized in that said metallic compress consists of sintered platinum.

6. The implantable electrode means as defined in claim 1 wherein a diffusion bond connects said filamentary compress to said electrically conductive lead member.

* * * * *